(12) United States Patent
Kowalewski et al.

(10) Patent No.: US 6,611,763 B2
(45) Date of Patent: Aug. 26, 2003

(54) METHOD OF EARLY PREDICTING PARAFFIN DEPOSITION RISKS DURING PRODUCTION AND TRANSPORT

(75) Inventors: Isabelle Kowalewski, Bailly (FR); Véronique Ruffier-Meray, Poissy (FR); Guillaume Guehenneux, Paris (FR); Alain-Yves Huc, Rueil-Malmaison (FR); Emmanuel Behar, Jouy le Moutier (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 86 days.

(21) Appl. No.: 09/814,002

(22) Filed: Mar. 22, 2001

(65) Prior Publication Data

US 2002/0050355 A1 May 2, 2002

(30) Foreign Application Priority Data

Mar. 24, 2000 (FR) .............................. 00 03867

(51) Int. Cl.$^7$ .............................................. G06F 19/00
(52) U.S. Cl. ...................... 702/13; 73/61.62; 73/152.42
(58) Field of Search ...................... 702/6, 13; 73/61.62, 73/152.42

(56) References Cited

U.S. PATENT DOCUMENTS 5,959,194 A * 9/1999 Nenniger ................... 73/61.62

* cited by examiner

*Primary Examiner*—Donald E. McElheny, Jr.
(74) *Attorney, Agent, or Firm*—Antonelli, Terry, Stout & Kraus, LLP

(57) ABSTRACT

Method of predicting paraffin deposition risks during hydrocarbon production and/or transport, applicable at an early reservoir characterization and production stage. It comprises forming a database characterizing the hydrocarbons in the formation, including density data acquired by well logging and data obtained by analysis of rock samples taken from the reservoir formation, an analytical representation of the hydrocarbons by a limited number of pseudo-components comprising each certain hydrocarbon classes with a definition of their respective mass fractions and application of data of said base to a thermodynamic model for determining one or more parameters indicative of the crystallization conditions such as, for example, the starting crystallization temperature, the solid fraction that precipitates when the temperatures falls below this starting crystallization temperature, etc. Applications: hydrocarbon production field valuation.

7 Claims, 4 Drawing Sheets

METHOD OF EARLY PREDICTING PARAFFIN DEPOSITION RISKS DURING PRODUCTION AND TRANSPORT

FIELD OF THE INVENTION

The present invention relates to a method of predicting paraffin deposition risks during hydrocarbon production and/or transport, applicable at an early reservoir characterization and production stage.

BACKGROUND OF THE INVENTION

Paraffins precipitation is a recurring problem in oil production. Late detection of the presence of paraffins in the oil in place in the reservoir, even in small amounts, can lead to very costly production problems (complete clogging of the production and/or transport pipes, wrong estimation of the producible reserves). In fact, during production, the cooling undergone by the hydrocarbons, either as they are expelled from the reservoir to the surface or as they are transported, leads in some cases to the crystallization of the paraffins. Similarly, degassing of the light fraction (<C10) of the fluid considered to be a good solvent of the high molecular weight molecules, which is linked with the pressure drop during production, favours paraffin deposition. Various known methods relative to the characterization of paraffins in production oils are described for example in the following documents:

Philp P., 1994, High temperature gas chromatography for the analysis of fossil fuels: a review, J. of High Res. Chromato., 17, 398–406, Philp P., Bishop A. N., Del Rio J. C. and Allen J., 1995, Characterization of high molecular weight hydrocarbons (>C40) in oils and reservoir rocks, The Geochemistry of Reservoirs, Geological Society Special Publication, 86, 71–75, Heath D., Lewis C. and Rowland S., 1997, The use of high temperature gas chromatography to study the biodegradation of high molecular weight hydrocarbons, Org. Geochem., 26, 769–786, Thanh N. X., Hsieh M. and Philp R. P., 1999, Waxes and asphaltenes in crude oils, Org. Geochem., 30, 119–132.

Patent FR-2,753,535 filed by the applicant describes a method for modelling the crystallization of paraffins in petroleum fluids according to the composition thereof, using an analytical representation of the petroleum fluids in form of pseudo-constituents in limited number comprising each certain hydrocarbon classes. From a database comprising the values of physico-chemical parameters of a certain number N of pure hydrocarbon constituents, the physico-chemical parameters of at least part of these pseudo-components are determined by combination of the corresponding physico-chemical parameters of these hydrocarbon constituents. Application of data from this base to a thermodynamic model allows to determine the wax or paraffin appearance temperatures.

Existing models work from input data obtained via analyses carried out at a late production stage, from stock-tank oils that have already lost the main part of the C40+ fraction if precipitation phenomena have already occurred in the reservoir or along production tubings. The signs that would allow a model to make an early prediction of the appearance of deposits are therefore missing from the experimental data collected.

SUMMARY OF THE INVENTION

The method according to the invention allows to predict paraffin deposition risks during production and/or transport at an early stage of characterization and production of an underground reservoir formation. It comprises forming a database characterizing the hydrocarbons in the formation, including density data acquired by well logging and data obtained by analysis of rock samples taken from the formation, an analytical representation of the hydrocarbons by a limited number of pseudo-components comprising each certain hydrocarbon classes with definition of the respective mass fractions thereof and application of data from said base to a thermodynamic model for determining one or more parameters indicative of the crystallization conditions such as, for example, the starting crystallization temperature and the solid fraction that precipitates when the temperatures falls below this critical temperature, etc.

The method comprises for example an analytical representation of the hydrocarbons in the formation by at least nine pseudo-constituents among which at least five pseudo-constituents concern the C14− fraction and the rest of the pseudo-constituents concerns the C14+ fraction.

The C14− fraction is for example represented by five pseudo-constituents, the first and the second (P1, P2) being representative of the n-alkanes whose number of carbon atoms is less than or equal to 14, the third one (P3) being representative of the iso-alkanes, the fourth one (P4) being representative of the naphthenes, and the fifth one (P5) being representative of the aromatics.

The C14+ fraction is for example represented by at least four pseudo-constituents, the first and the second (P6, P7) being representative of the n-alkanes whose number of carbon atoms is above 14, the third one (P8) being representative of the non n-paraffinic saturates and the fourth one (P9) being representative of the unsaturates. For the rock sample, insofar as analysis of the normal paraffins is continued up to the C70, the normal paraffins between C40 and C70 can be considered individually.

The method comprises for example, from the sample fluid analysis results, for the third and the fourth pseudo-constituents (P8, P9) comprising the heavier fractions, creating respectively two fictitious molecules defined each by a molar distribution among the various groups that constitute it and connected together by a determined mass relation, and calculating the thermodynamic properties thereof.

The paraffin deposits formed are for example likened to a non-ideal single solid phase that can be modelled by a parameter that represents the binary interactions in the solid phase.

Collection of the experimental data obtained by density logging measurements and rock sample analyses allows finer characterization of the fluids in the formation and notably of the heavy paraffin fraction (>C40+) which is mainly responsible for the crystallization thereof and it allows to better constrain the thermodynamic simulation model used to predict the parameters of this phenomenon.

BRIEF DESCRIPTION OF THE DRAWINGS

Other features and advantages of the method according to the invention will be clear from reading the description hereafter, with reference to the accompanying drawings wherein.

DETAILED DESCRIPTION

I Measurements and Analyses

The method first comprises characterizing the hydrocarbons in the reservoir from data obtained by well logging allowing to determine the density of the hydrocarbons in the reservoir on the one hand, and by analysis of core samples taken in situ on the other hand.

I-1 Core Measurements

Figure 1:
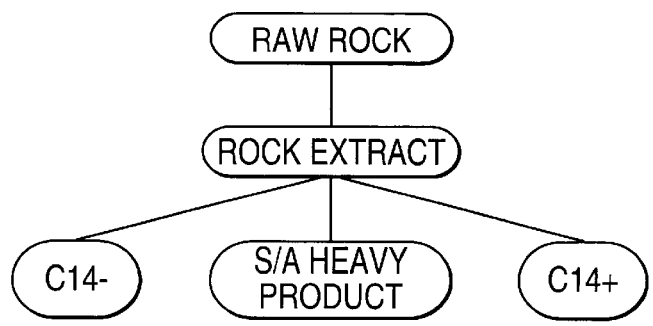
FIG. 1 illustrates the core sample analysis process.

As shown in FIG. 1, the data to be applied to the thermodynamic model are obtained by:

a) extraction, by means of a known extraction technique, of the hydrocarbons from the rock fragments taken from cores, and b) fractionation of the extract into two parts: the C14− and the C14+ fractions, that are analyzed separately.

Analysis of the C14− Fraction

The C14− fraction is analyzed by quantitative gas chromatography (GC) preferably according to the <<Carburane>> method described by:

Durand J. P., et al, <<Direct and Automatic Capillary GC Analysis for Molecular Weight Determination and Distribution in Crude Oils and Condensates up to C20>>, J. of High Resolution Chromatography, 12, 1989, p.230.

This type of petroleum fluid analysis leads to the complete identification of all the hydrocarbons up to nC11, of all the n-alkanes up to nC20, to the distribution among the iso-alkanes, the naphthenes and the aromatics by fraction of a carbon atom between nC11 and nC15, and to a distribution among the saturates and the aromatics by fraction of a carbon atom between nC15 and nC20.

Analysis of the C14+ Fraction

The analytical quantities to be acquired on the C14+ fraction are: the distribution of the n-alkanes up to the greatest carbon atom number possible, the molar mass of the fraction, and the distribution among the saturates, the aromatics, the resins and the asphaltenes or the heavy products (resins+asphaltenes).

The following quantities have been measured for developping the thermodynamic model:

1) the distribution of the n-paraffins by gas chromatography (GC) up to nC40 or more (depending on the chromatographic technique used), 2) the molar mass of the C14+ fraction, for example by tonometry, or estimated from the chromatographic analysis of the C14+ fraction, or by gel-permeation chromatography, 3) the proportion between the saturates, the aromatics and the heavy products by thin-layer or liquid chromatography of the C14+ fraction. The S.A./heavy products, i.e. the distribution in weight percent among each one of these chemical families, is thus obtained for this fraction.

1-2 Well Logging Measurements—GOR Determination

If it is not known otherwise, the density of the C14− fraction (and therefore the quantity) can be estimated by means of logging measurements. The total density of the hydrocarbons present in the reservoir can be evaluated from logs obtained during drilling, which requires neutron/density, resistivity measurement or NMR techniques, or the technique known to the man skilled in the art, referred to as <<Saraband>>, described for example in the following publications:

Frank R. W., <<Formation Evaluation With Logs in The Ark-La-Tex Cotton Valley, Trans Gulf Coast>>, Ass. Geol. Soc., 28(1), p.131–141, 1978, Ratliff J. R. et al, <<Applications of the Saraband sand-shale technique in North America States>>, Transactions of the SPWLA Annual Logging Symposium, ed. Society of Professional Well Log Analysts, Houston, Tex., United, 12, p.1–23, Diatschenko V., <<Downhole Fluid-Density Measurement in the Presence of Radially Separated Liquids>>, Log. Anal., 33(1), p.67–74, 1992, Morris C. W. et al, <<Using optical fluid analysis to evaluate downhole fluid sample contamination>>, Spe. Petroleum Conference, The Hague, Proceedings, p.283–295, 1998, or Latorraca G. A. et al, <<Low-Field NMR Determination of the Properties of Heavy Oils and Water-in-Oil Emulsions>>, $4^{th}$ Sintef Et Al Recent Advances in Magnet. Resonance App. to Porous Media Int. Meeting, Trondheim, Norway, Magnet. Resonance Imaging, 16 (5–6), p.659–662, 1998.

Knowing the density of the fluid in the reservoir and the density of the fluids that are extracted from the rock samples and analyzed as described hereafter, the density of the light fraction can be deduced therefrom and an evaluation of the GOR can thus be obtained.

In the most unfavourable cases, it is possible to use the GOR values obtained for already developped neighbouring fields (regional data) to evaluate the density.

Figure 2:
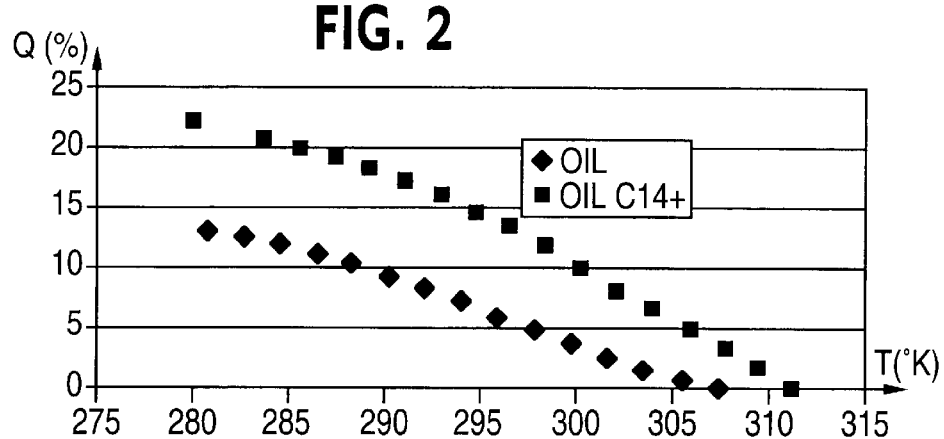
FIG. 2 shows the influence of the light fraction on the starting crystallization temperature calculated by the model.

However, if this value is not accessible, the model will determine crystallization temperatures with errors greater than or equal to 5° C. FIG. 2 shows the influence of the light fraction on the crystallization temperature calculated by the model. The results show that the crystallization temperature is overestimated if the C14− fraction, which acts as a solvent for high molecular weight paraffins, is not taken into account.

II Thermodynamic Modelling

The thermodynamic model that is used in the description hereafter is similar to the model already described in the aforementioned patent FR-2,753,535. It is however described below for clarity reasons.

A thermodynamic model intended to represent each phase has to be selected to calculate the gas, liquid, solid equilibria. At determined temperatures and pressures, the molar ratio between the various solid (S), liquid (L) and gas (G) phases is sought for a crude having a given composition.

The liquid (L)/gas (G) and solid (S)/liquid (L) equilibrium conditions of a system consisting of n constituents at equilibrium are written, on which the calculations relative to the solid deposits of paraffinic crudes are based. At thermodynamic equilibrium, the fugacity fi of component i must be equal in the three phases:

$$f_i^S = f_i^L = f_i^G.$$

The fugacities of the liquid and of the gas of component i are expressed as follows:

$$f_i^L(T, P, x_i^L) = P * x_i^L * \varphi_i^L(T, P, x_i^L) \tag{A3}$$

$$f_i^G(T, P, x_i^G) = P * x_i^G * \varphi_i^G(T, P, x_i^G) \tag{A4}$$

where $x_i^L$, $x_i^G$, $x_i^S$ respectively represent the molar fractions of i in the liquid, gas and solid phases.

The fugacity coefficients in the gas and liquid phases are calculated by means of Abdoul and Péneloux's group contribution method described for example in:

Abdoul W., Rauzy E., Peneloux A., (1991), <<Group-Contribution Equation of State for Correlating and Predicting Thermodynamic Properties of Weakly Polar and Non-Associating Mixtures. Binary and Multi-Component Systems>>. Fluid Phase Equilibria, 69, pp.47–102.

The fugacities in the solid phase are expressed as a function of the activity coefficients $\gamma_i^S$:

$$f_i^S(T, P, x_i^S) = x_i^S * f_i^S(T, P_{ref}) * \gamma_i^S(T, P_{ref}, x_i^S) * \exp\int_{P_{ref}}^{P} \frac{\overline{v}_i^S}{RT} * dP \tag{A5}$$

$P_{ref}$ is a reference pressure, $\overline{v}_i$ is the partial molar volume, defined as follows (with V the volume of the system considered and $n_i$ the number of moles of constituent i):

$$\overline{v}_i = \left(\frac{\partial V}{\partial n_i}\right)_{T,P,n_{j\neq i}} \tag{A6}$$

The expression of the liquid/gas and solid/liquid partition constants $K_i^{LG}$ and $K_i^{SL}$ is deduced therefrom:

$$K_i^{LG} = \frac{x_i^L}{x_i^G} = \frac{\varphi_i^G(T, P, x_i^G)}{\varphi_i^L(T, P, x_i^L)} \tag{A7}$$

$$K_i^{SL} = \frac{x_i^S}{x_i^L} = \frac{P * \varphi_i^L(T, P, x_i^L)}{f_i^S(T, P_{ref})} * \frac{\exp\int_{P_{ref}}^{P} \frac{-\overline{v}_i^S}{RT} * dP}{\gamma_i^S(T, P_{ref}, x_i^S)} \tag{A8}$$

If we consider that there is a solid $S_1$—solid $S_2$ phase transition, Equation A8 is written in the following known form:

$$\ln\frac{f_i^{Ls}(T, P_{ref})}{f_i^S(T, P_{ref})} = \tag{A9}$$

$$\frac{\Delta g_i^{S \rightarrow Ls}}{RT} = \frac{\Delta h_i^{fusion}}{RT} * \left(1 - \frac{T}{T_i^{fusion}}\right) + \frac{\Delta h_i^{S-S}}{RT} * \left(1 - \frac{T}{T_i^{S-S}}\right) +$$

$$\frac{C_{p_i}^{Ls} - C_{p_i}^{S_1}}{R} * \left(\ln\frac{T_i^{fusion}}{T_i^{S-S}} + \frac{T_i^{S-S} - T_i^{fusion}}{T}\right) +$$

$$\frac{C_{p_i}^{Ls} - C_{p_i}^{S_2}}{R} * \left(\ln\frac{T_i^{S-S}}{T} + \frac{T - T_i^{S-S}}{T}\right) \text{ and}$$

$$f_i^{Ls}(T, P_{ref}) = P * \varphi_i^{Ls}(T, P_{ref}) \tag{A10}$$

where $T_i^{fusion}$, $T_i^{S-S}$, $\Delta h_i^{S-S}$ are the fusion and solid—solid transition temperatures and enthalpies. $C_{p_i}^{Ls}$, $C_{p_i}^{S_1}$, $C_{p_i}^{S_2}$ are the heat-capacity rates of a constituent i respectively in the <<supercooled liquid>> phase and in the solid phase in its crystalline forms $S_1$ or $S_2$.

We thus obtain, for solid/liquid partition constant $K_i^{SL}$, the following expression:

$$K_i^{SL} = \frac{x_i^S}{x_i^L} = \frac{\varphi_i^L(T, P, x_i^L)}{\varphi_i^{Ls}(T, P_{ref})} * \frac{\exp\int_{P_{ref}}^{P} \frac{-\overline{v}_i^S}{RT} * dP}{\gamma_i^S(T, P_{ref}, x_i^S)} * \exp\left(\frac{\Delta g_i^{S \rightarrow Ls}}{RT}\right) \tag{A11}$$

The analyses described above and the logging measurements lead to a set of experimental data that provide more information and are more representative of the real content of the reservoir than those obtained from usual analyses from stock-tank oils. Some of the data that are effectively applied as input data to the thermodynamic model described above are direct experimental data or data elaborated therefrom.

Pseudo-constituents

The thermodynamic model used being of molecular compositional type, it requires knowledge of the molar composition of the reservoir fluids, whether produced crudes or fluids extracted from cores, and therefore a considerable amount of data since, in these extracted crudes or fluids, hundreds of different hydrocarbons can be identified. It is impossible in practice to consider all of these data because the physico-chemical quantities (Tc, Pc, ω, fusion temperatures and enthalpies, etc.) concerning notably the non <<n-paraffinic>> compounds are not known from the moment that their number of carbon atoms is above 10, and the required calculation time would be too long for the industrial applications of the model.

Therefore, all of the hydrocarbons, whether all of the constituents that are perfectly identified by gas chromatography or all those for which only the number of carbon atoms and the chemical family are known, have been grouped together into a certain number of groups or pseudo-constituents.

We have chosen to represent the hydrocarbons of the reservoir preferably by at least 9 pseudo-constituents among which at least five concern the C14– fraction and the rest (at least four) concern the C14+ fraction. For the rock extracts, since the chromatographic analyses show the presence of much heavier paraffins, they are preferably identified as such in the model.

The C14– fraction is represented by 5 pseudo-constituents P1, P2, P3, P4 and P5 or more. In the case of 5 pseudo-constituents P1, P2, P3, P4 and P5, they are defined as follows:

P1 and P2 represent the n-alkanes whose number of carbon atoms is less than or equal to 14, P3 is the pseudo-constituent representative of the iso-alkanes in the C14− fraction, P4 is the pseudo-constituent representative of the naphthenes in the C14− fraction, P5 is the pseudo-constituent representative of the aromatics in the C14− fraction.

In order to determine the starting crystallization temperature and the amount of deposit as a function of the temperature, it is necessary to know a certain number k of physico-chemical parameters or quantities specific to each pseudo-constituent representative of the fluid studied, nine in number for example:

1. molar mass, MM;
2. fusion temperature, $T_{fusion}$;
3. solid—solid transition temperature, $T_{SS}$;
4. fusion enthalpy, $\Delta h_{fusion}$.
5. solid—solid transition enthalpy, $\Delta h_{SS}$;
6. critical temperature, $T_c$;
7. critical pressure, $P_c$;
8. acentric factor, $\omega$;
9. molecular conformation parameter, $l_i$.

The method comprises forming a database in which the physico-chemical parameters or quantities defined above, relative to a number N of pure hydrocarbons (N=95 for example), have been grouped together. It is from these pure hydrocarbons that the corresponding physico-chemical parameters assigned to at least part of the pseudo-constituents are calculated.

For each pseudo-constituent of the C14− fraction, the k quantities $G_d(P,j)$ are calculated according to the following relation:

$$G_d(P, j) = \frac{\sum_{i=1}^{\tau} x_i * G_d(i, j)}{\sum_{i=1}^{\tau} x_i} \quad (3)$$

where:

$\tau$ is the number of hydrocarbons represented by pseudo-constituent P, $x_i$ the mole percent in the rock extract of the i-th hydrocarbon (i=1, . . . , $\tau$) represented by pseudo-constituent P, $G_d(i,j)$ the j-th property from among the 9 or more mentioned above of the i-th hydrocarbon, $G_d(P,j)$ the j-th property from among the 9 or more mentioned above of pseudo-constituent P.

When the molar masses of each one of the pseudo-constituents have been calculated, their mole percent in the rock extract is obtained from the mass percents.

The C14+ fraction is represented by 4 pseudo-constituents P6, P7, P8 and P9 or more and, for example, the normal paraffins between C40 and C60. In the case of 4 pseudo-constituents P6, P7, P8 and P9, they are defined as follows:

P6 and P7 represent the n-alkanes whose number of carbon atoms is above 14,

P8 is the pseudo-constituent representative of the non n-paraffinic saturates (all of the iso-alkanes and of the naphthenes) in the C14+ fraction, P9 is the pseudo-constituent representative of the unsaturated molecules (aromatics, resins, asphaltenes) in the C14+ fraction.

For pseudo-constituents P8 and P9, the following analytical information is available:

mass distribution among the various chemical families: saturates and aromatics, and resins or heavy products; and possibly structural units by NMR of the $^{13}C$ of each one of these families.

The method also comprises creating, for each pseudo-constituent P8, P9, a fictitious molecule characterized by its molar distribution among the various groups that constitute it.

This distribution allows to define pseudo-constituents P8 and P9 and to calculate their physico-chemical properties (Tc, Pc, $\omega$, etc.), provided that their molar mass ($MM_{P8}$ and $MM_{P9}$ respectively) and their number of carbon atoms ($C_{P8}$ and $C_{P9}$) are known.

The crude analysis results gathered in the database also allow, besides determination of the two fictitious molecules, to establish a relation between the molar mass of P8 and that of P9:

$$MM_{P8} = 1.33 * MM_{P9} \quad (5)$$

Knowing the molar mass of the C14+ fraction: $MM_{C14+}$, the weight percent in the rock extract of pseudo-constituent P8<<non n-paraffinic saturates>> and that of pseudo-constituent P9 non-saturated with C14+, molar masses $MM_{P8}$ and $MM_{P9}$ are respectively determined by means of Equation (5) and of Equation (6) as follows:

$$MM_{C14+} = \frac{p(P6) + p(P7) + p(P8) + p(P9)}{\frac{p(P6)}{MM_{P6}} + \frac{p(P7)}{MM_{P7}} + \frac{p(P8)}{MM_{P8}} + \frac{p(P9)}{MM_{P9}}}$$

Pi: pseudo-constituent No.i (i=1, . . . , 9), p(Pi): weight percent in the rock extract of pseudo-constituent Pi, $MM_{Pi}$: molar mass of pseudo-constituent Pi.

The data relative to the pseudo-constituents representative of the n-alkanes in the C14+ fraction being known (P6 and P7), Equations (5) and (6) allow to calculate unknowns $MM_{P8}$ and $MM_{P9}$.

From the empirical formula of the fictitious molecules of P8 and P9, the following ratio can be obtained:

$$Rpi = \frac{\text{number of hydrogen atoms of pseudo-constituent Pi}}{\text{number of carbon atoms of pseudo-constituent Pi}}$$

We thus obtain: RP8=1.88 and RP9=1.2332.

The numbers of carbon atoms $C_{P8}$ and $C_{P9}$ are determined according to Equations (7) and (8):

$$C_{P8} = \frac{MM_{P8}}{MM_C + RP8 * MM_H} \quad (7)$$

$$C_{P9} = \frac{MM_{P9}}{MM_C + RP9 * MM_H} \quad (8)$$

with:

$MM_C$ the atomic mass of carbon (close to 12 g), and $MM_H$ the atomic mass of hydrogen (close to 1 g).

Determination of the Physico-chemical Quantities of Pseudo-constituents P8 and P9

For pseudo-constituents P8 and P9, which are not generated from identified hydrocarbons, it is necessary to calculate the nine physico-chemical properties and to enter them into the data file. In order to calculate all the physico-chemical quantities of these pseudo-constituents by means of group contribution methods, it is necessary to calculate first quantity No.9, i.e. the parameters of Abdoul and Peneloux's model (1987) described in the following publication:

Abdoul W. et al (1991), <<Group-Contribution Equation of State for Correlating and Predicting Thermodynamic Properties of Weakly Polar and Non-Associating Mixtures. Binary and Multi-Component Systems>>. Fluid Phase Equilibria, 69, pp.47–102.

From the numbers of groups of fictitious molecules, the respective numbers of carbon atoms $C_{Pi}$ (i=8 or 9) of pseudo-constituents Pi, the number N(Pi) of the constitutive groups of each pseudo-constituent is calculated by the relation:

$$N(Pi) = C_{Pi}/100 * \text{Number of groups of the fictitious molecule of } Pi.$$

For the rock extract, the pseudo-constituents are calculated in the same way, except for the normal paraffins above NC40 that are considered individually. The database of the model also contains their characteristic quantities.

Adjustment of the Parameter of Binary Interaction in the Solid Phase

Adjustment of the parameter of binary interaction in the solid phase is performed substantially as mentioned in the aforementioned patent filed by the applicant. To implement this method, the deposits formed are likened to a non ideal single solid phase and the excess free enthalpy of this phase is expressed by means of an empirical relation whose parameter(s) can be adjusted to the experimental results (in particular the solid deposit curve). The one-parameter equation proposed by Margules, which is well-known to specialists, is selected therefore. It affords the advantage of having the simplest expression possible among those giving the excess free enthalpy:

$$g^E = \sum_{i=1}^{n} \sum_{j=i+1}^{n} A_{ij}(T) * x_i^S * x_j^S \quad (A12)$$

where $A_{ij}$ is the parameter of binary interaction in the solid phase between constituents i and j. Knowing function $g^E$ allows to calculate the coefficients of activity in the solid phase:

$$RT \ln \gamma_i^S = \left( \frac{\partial n g^E}{\partial n_i} \right)_{T,P,n_j} = -g^E + \sum_{j=1, j \neq i}^{n} A_{ij}(T) * x_j^S \quad (A13)$$

It is considered that the parameters of binary interaction in the solid phase are all identical and equal to parameter A, i.e.:

$$\begin{cases} A_{ij} = A_{ji} = A \text{ with } i \neq j \\ \text{and} \\ A_{ii} = 0 \end{cases} \quad (A14)$$

We thus obtain the following expression for the solid/liquid partition constants:

$$K_i^{SL} = \frac{x_i^S}{x_i^L} = \frac{\varphi_i^L(T, P, x_i^L)}{\varphi_i^{LS}(T, P_{ref})} * \frac{\exp(\Delta g_i^{S \to L_S}/RT)}{\gamma_i^S(T, P_{ref}, x_i^S)} \quad (A15)$$

where:

$$\frac{\Delta g_i^{S \to L_S}}{RT} = \frac{\Delta h_i^{fusion}}{RT} * \left(1 - \frac{T}{T_i^{fusion}}\right) + \frac{\Delta h_i^{S-S}}{RT} * \left(1 - \frac{T}{T_i^{S-S}}\right) \quad (A16)$$

and where the $\gamma_i^S$ are given by Equations (A12) to (A14).

Partition constants $K_i^{LG}$ (Equation A7) and $K_i^{SL}$ (Equation A15) allow to have access to the molar compositions $x_i$ of each constituent in each phase at equilibrium and therefore to the desired ratio (i.e. the ratio in number of moles of the amount of solid deposits S to the total number of moles of fluid F in the reservoir).

Figure 3:
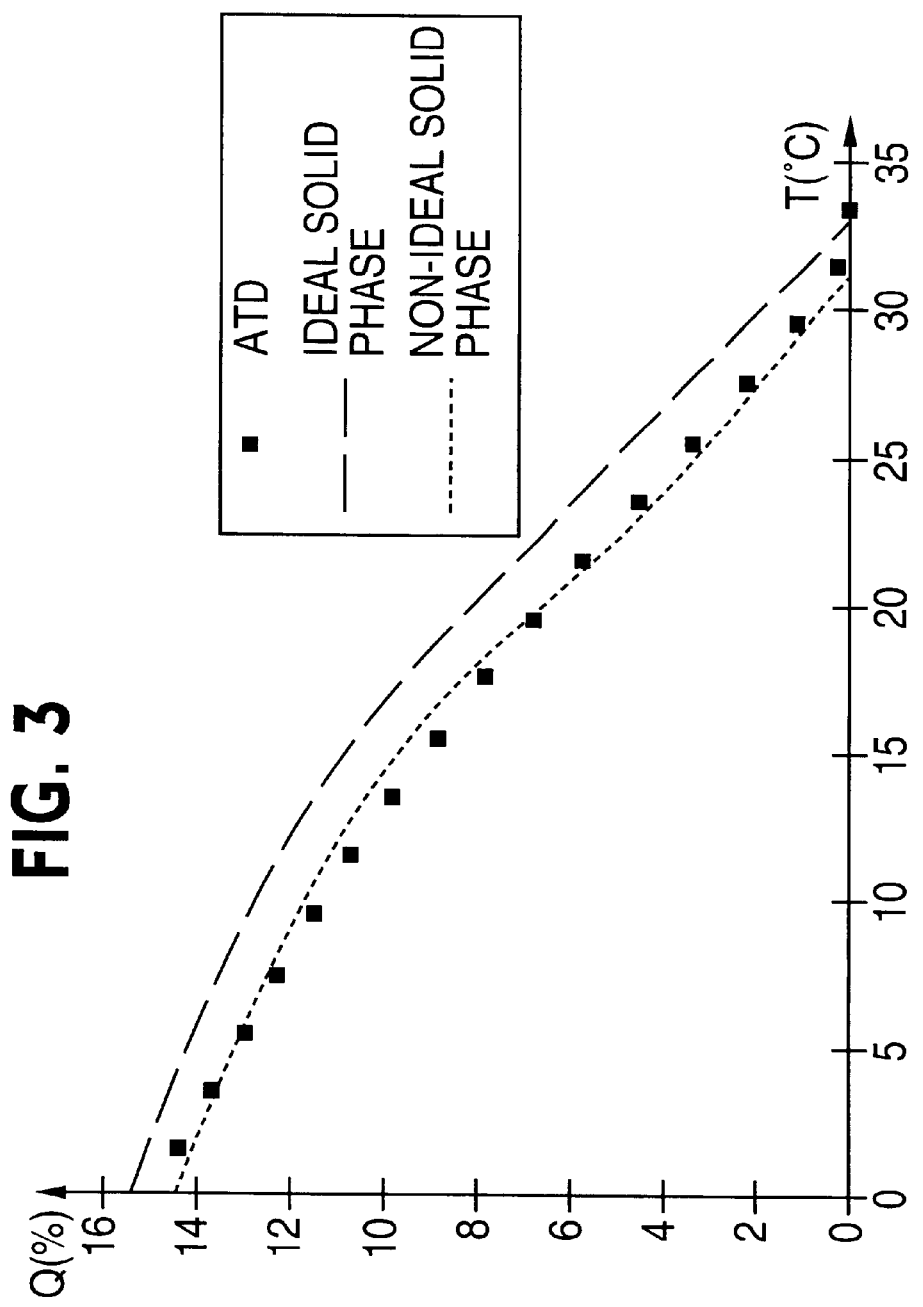
FIG. 3 shows a comparison of the calculated and experimental solid deposit curves obtained by means of a NMR technique.
Figure 4:
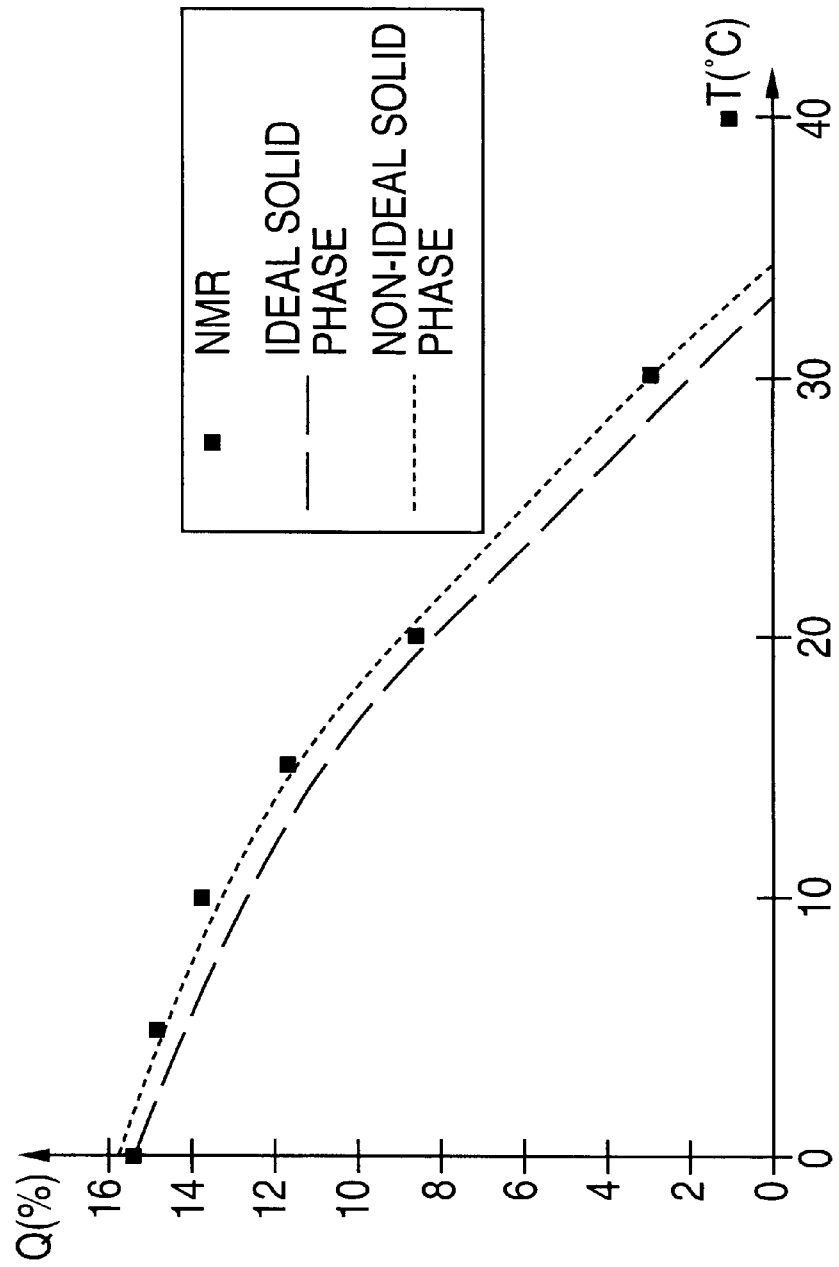
FIG. 4 shows a comparison of the calculated and experimental solid deposit curves obtained by means of a technique referred to as DTA.
Figure 5:
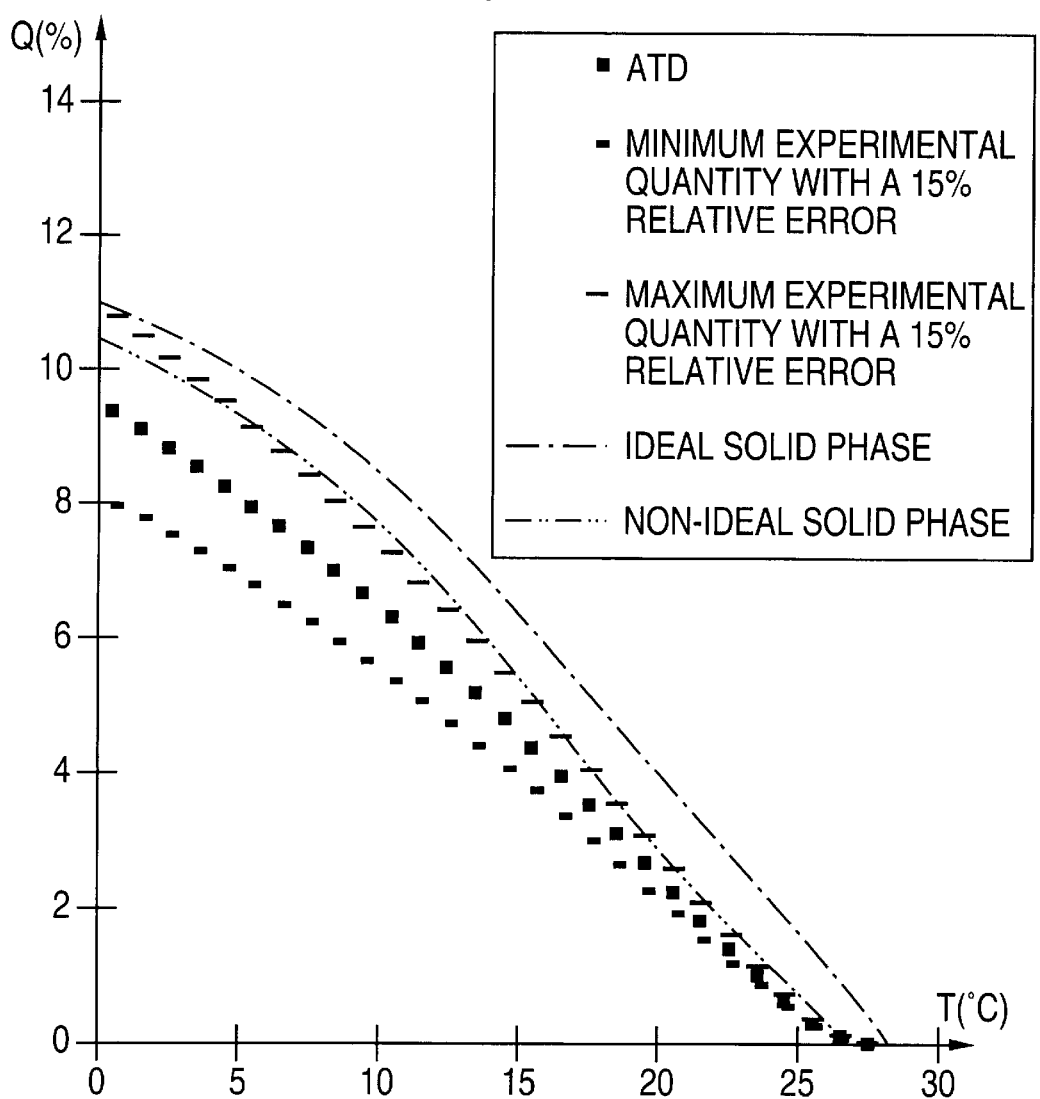
FIG. 5 shows a comparison of the calculated and experimental solid deposit curves obtained by means of the DTA technique in the case of a crude fluxed by addition of a light condensate.

The modelling equation with one parameter A used only requires adjustment of one parameter A which represents the binary interactions in the solid phase. It has been checked that the results calculated with this equation to represent the solid phase are in accordance with the experimental results (FIGS. 3, 4). This parameter is identical for all the binaries involved in the solid mixture. Knowing parameter A allows to calculate the solid deposit curves of the fluids whose composition has slightly varied (through addition of a fluxing agent for example, as illustrated in FIG. 5).

Adjustment of A is performed from the solid deposit curve measured in the laboratory with the original rock extract. It is carried out by means of a least-squares method on all the points of the curve.

III Validation on an Applied Case

Figure 6:
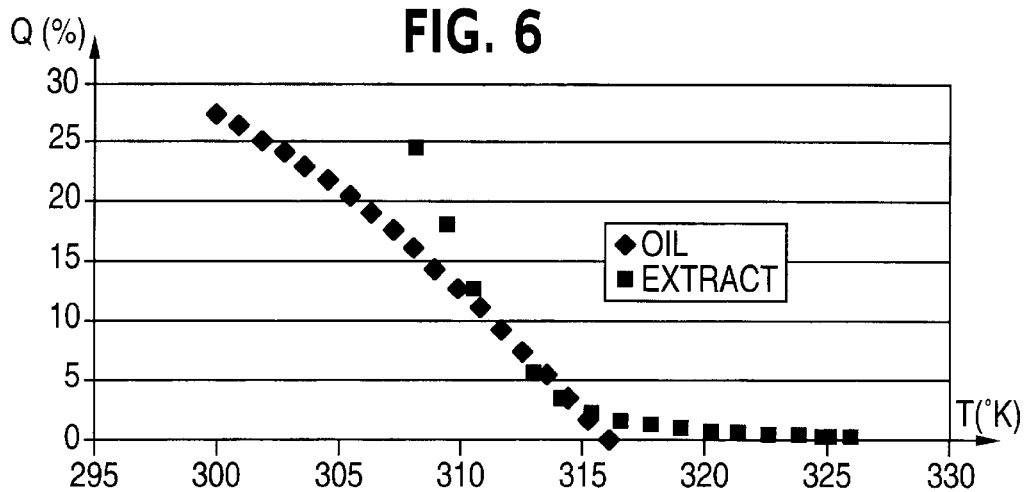
FIG. 6 shows the solid deposit curve calculated for an oil sample and a rock sample.

This method has been applied to a field P exhibiting organic deposits appeared during production in the vicinity of the wellhead. The production oil and the core extract from the reservoir have therefore been studied to obtain the data required for the thermodynamic model. FIG. 6 shows the modelling results. If the predictive calculation is made from the analytical data collected on an oil sample taken from stock-tank oil, the calculated starting crystallization temperature is then 42° C. On the other hand, if the data used are those obtained from the reservoir core extract, the calculated crystallization temperature is 52° C. Calculation shows that the starting crystallization temperature of paraffins is significantly underestimated if the prediction is made on the stock-tank oil after bringing in the well (the paraffins have already deposited). On the other hand, this risk of deposition during production could have been anticipated if the prediction had been made before production on the core sample.

The advantage of the method then appears clearly:
the prediction can be made at a very early stage (before production), which allows a much more reliable technico-economic evaluation. The means to be used for production can be optimized;
the estimate obtained is more precise since almost all of the heavy normal paraffins, responsible for the formation of deposits, are identified and taken into account in the model, hence a better estimation of the producible reserves in place. The amount of paraffins that will accumulate during production can also be estimated.

What is claimed is:

1. Method of predicting paraffin deposition risks at an early stage of characterization of an underground formation and/or during production, characterized in that it comprises forming a database characterizing hydrocarbons in the formation, including density data acquired by well logging and data obtained by analysis of rock samples taken from the formation, analytical representation of the hydrocarbons by a limited number of pseudo-constituents comprising each certain hydrocarbon classes with definition of the respective mass fractions thereof and application of data of said base to a thermodynamic model suited to determine one or more parameters indicative of the crytallization conditions such as, for example, the starting crystallization temperature or the solid fraction that precipitates when the temperature falls below this critical temperature.

2. Method as claimed in claim 1, characterized in that the model is suited to determine the crystallization temperature of the hydrocarbons or the mass fraction that precipitates below the crystallization temperature.

3. Method as claimed in claim 1, characterized in that the hydrocarbons in the formation are analytically represented by at least nine pseudo-constituents among which at least five pseudo-constituents concern the C14− fraction and the rest of the pseudo-constituents concerns the C14+ fraction.

4. Method as claimed in claim 3, characterized in that the C14− fraction is represented by five pseudo-constituents, the first and the second (P1, P2) being representative of the n-alkanes whose number of carbon atoms is less than or equal to 14, the third one (P3) being representative of the iso-alkanes, the fourth one (P4) being representative of the naphthenes and the fifth one (P5) being representative of the aromatics.

5. Method as claimed in claim 3, characterized in that the C14+ fraction is represented by at least four pseudo-constituents, the first and the second (P6, P7) being representative of the n-alkanes whose number of carbon atoms is above 14, the third (P8) being representative of the non n-paraffinic saturates and the fourth (P9) being representative of the unsaturates.

6. Method as claimed in claim 5, characterized in that, from fluid sample analysis results, two fictitious molecules defined each by a molar distribution among the various groups that constitue it and connected by a determined mass relation are respectively created for the third and the fourth pseudo-constituents (P8, P9) comprising the heavier fractions, and the thermodynamic properties thereof are calculated.

7. Method as claimed in claim 1, characterized in that the paraffin deposits formed are likened to a non-ideal single solid phase that can be modelled by a parameter (A) which represents the binary interactions in the solid phase.

* * * * *